(12) United States Patent
Sawrey

(10) Patent No.: US 8,222,460 B2
(45) Date of Patent: Jul. 17, 2012

(54) PROCESS FOR THE PRODUCTION OF MIBC AND /OR IBHK PLUS TMN USING COPPER-BASED CATALYSTS

(75) Inventor: Jeffrey Scott Sawrey, Westford, MA (US)

(73) Assignee: Dow Global Technologies LLC, Midland, MI (US)

( * ) Notice: Subject to any disclaimer, the term of this patent is extended or adjusted under 35 U.S.C. 154(b) by 154 days.

(21) Appl. No.: 12/670,195

(22) PCT Filed: Jul. 17, 2008

(86) PCT No.: PCT/US2008/070262
§ 371 (c)(1),
(2), (4) Date: Jun. 25, 2010

(87) PCT Pub. No.: WO2009/017970
PCT Pub. Date: Feb. 5, 2009

(65) Prior Publication Data
US 2010/0317897 A1 Dec. 16, 2010

Related U.S. Application Data

(60) Provisional application No. 60/952,322, filed on Jul. 27, 2007.

(51) Int. Cl.
*C07C 45/73* (2006.01)
*C07C 29/145* (2006.01)

(52) U.S. Cl. ........................................ 568/388; 568/881

(58) Field of Classification Search .................. 568/388, 568/881
See application file for complete search history.

(56) References Cited

U.S. PATENT DOCUMENTS

| 2,137,407 A | 11/1938 | Lazier |
| 3,657,351 A | 4/1972 | Araki et al. |
| 5,925,796 A | 7/1999 | Bassett et al. |
| 6,518,462 B2 | 2/2003 | Saayman et al. |
| 6,706,928 B2 | 3/2004 | Kelly |
| 6,762,328 B2 | 7/2004 | Saayman et al. |
| 6,977,314 B2 | 12/2005 | Vandersall et al. |

FOREIGN PATENT DOCUMENTS

WO 2007/038440 A1 4/2007

OTHER PUBLICATIONS

Torres, et al., "One-step methl isobutyl ketone (MIBK) synthesis from 2-propanol: Catalyst and reaction condtion optimization", Applied Catalysis A: General, vol. 317, 2007 (pp. 161-170).

*Primary Examiner* — Sikarl Witherspoon
(74) *Attorney, Agent, or Firm* — Whyte Hirschboeck Dudek SC

(57) ABSTRACT

MIBC and/or a mixture of IBHK and TMN is produced from MIBK by a process comprising the step of contacting MIBK with hydrogen under condensation/hydrogenation/dehydration reactive conditions and in the presence of a catalytic amount of a Cu-based condensation/hydrogenation/dehydration catalyst. The relative amounts of MIBC and the mixture of IBHK and TMN are controlled by the reaction temperature, a lower temperature, e.g., 130 C., favoring MIBC alone, and a higher temperature, e.g., 200 C., favoring a mixture of MIBC and IBHK plus TMN.

10 Claims, 4 Drawing Sheets

FIG. 6
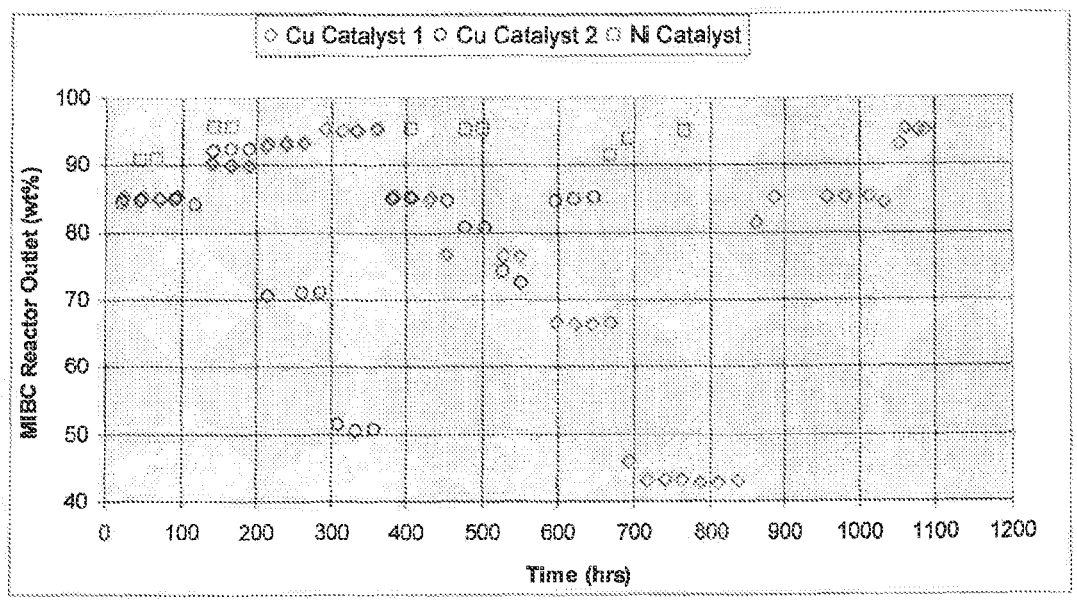
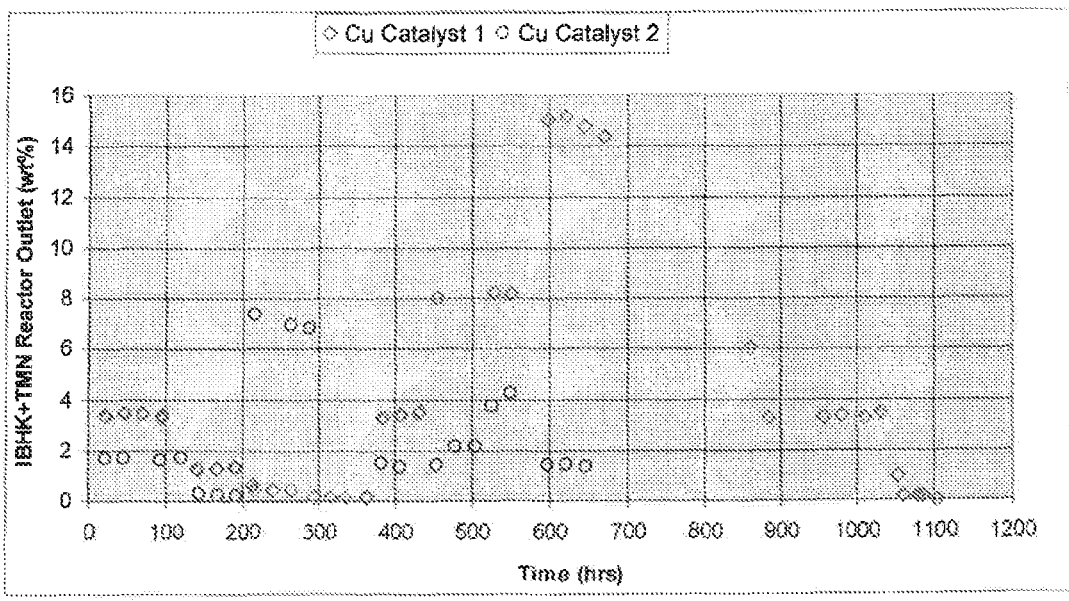
FIG. 7

PROCESS FOR THE PRODUCTION OF MIBC AND /OR IBHK PLUS TMN USING COPPER-BASED CATALYSTS

CROSS-REFERENCE TO RELATED APPLICATION

This application which claims the benefit of U.S. Provisional Application No. 60/952,322 filed Jul. 27, 2007, the teachings and disclosures of which are incorporated herein by reference.

FIELD OF THE INVENTION

This invention relates to a process for the production of solvents. In one aspect, the invention relates to a process for producing methyl isobutyl carbinol (MIBC) and a mixture of isobutyl heptyl ketone (IBHK) and trimethyl nonanol (TMN) while in another aspect, the invention relates to a process for making these solvents using a copper-based catalyst. In still another aspect, the invention relates to a process for making MIBC alone or in combination with a mixture of IBHK and TMN.

BACKGROUND OF THE INVENTION

The condensation of acetone and/or isopropanol to higher ketones is well known. For example, U.S. Pat. No. 6,977,314 discloses the condensation of acetone to methyl isobutyl ketone (MIBK) with a catalyst consisting of a polysulfonated ion exchange resin containing metal ions. U.S. Pat. No. 6,762,328 and U.S. Pat. No. 6,518,462 disclose a process to make MIBK by reactive distillation. In a first step acetone is condensed to mesityl oxide (MSO). In a second step MSO is hydrogenated to MIBK and small amounts of MIBC (also known as methylamyl alcohol). U.S. Pat. No. 6,706,928 discloses a vapor condensation process to convert acetone to MSO followed by hydrogenation of MSO to MIBK. This patent also discloses a single step condensation/hydrogenation process of acetone to MIBK. U.S. Pat. No. 5,925,796 discloses feeding MIBC and/or MSO with acetone and/or isopropanol to a multifunctional condensation/hydrogenation/dehydration catalyst in order to adjust the MIBK to DIBK (diisobutyl ketone) ratio in the product.

In one known process, MIBK, MIBC, DLBK and IBHK are co-produced in parallel, mixed ketone converters. Isopropanol and hydrogen are fed to the reaction system and through a series of condensation/hydrogenation/dehydration steps, the various products are generated. These condensation/hydrogenation/dehydration reactions can be carried out using a single multifunctional catalyst comprising copper, chromium and calcium carried on an aluminum oxide support. These products can be produced in specified amounts on a continuous basis. The ratio of products can be adjusted to a limited extent by altering the reaction conditions. The reaction chemistry for making these products is shown in FIG. 1.

Additional MIBC is produced by feeding refined MIBK produced in the mixed-ketone converters to a separate single hydrogenation converter containing a nickel-based catalyst.

IBHK is made in parallel by reaction 6 schematically shown in FIG. 1. Optionally, IBHK can be made in isolated campaigns. This is done by feeding MIBK and MIBC at high temperature (240 C) over a single multifunctional catalyst comprising copper, chromium and calcium carried on an aluminum oxide support. IBHK is partially hydrogenated in situ to its corresponding alcohol TMN (the hydrogen is ultimately derived from the dehydrogenation of IPA), thus producing a near equilibrium mixture of IBHK and TMN.

Of continuing interest is a process to increase the IBHK plus TMN capacity while eliminating the need for separate, labor intensive campaigns. Also of interest is a process that has a lower conversion cost and fewer hydrocarbon impurities, and eliminates concerns associated with the conventionally used, more expensive Ni-catalysts.

SUMMARY OF THE INVENTION

MIBC is produced and/or simultaneously co-produced with IBHK plus TMN by feeding MIBK and hydrogen over a Cu-based hydrogenation or multifunctional catalyst at low temperature conditions similar to those used with a Ni-based hydrogenation catalyst. In contrast to the process in which MIBC is produced in a converter using a nickel-based catalyst, the process of this invention allows for a dramatic increase the IBHK plus TMN capacity, eliminates the need for separate labor intensive campaigns to supplement IBHK plus TMN production, utilizes a much less expensive catalyst, lowers conversion costs and produces fewer hydrocarbon impurities.

In one embodiment. MIBC and/or a mixture of IBHK and TMN is produced from MIBK by a process comprising the step of contacting MIBK with hydrogen under condensation/hydrogenation/dehydration reactive conditions and in the presence of a catalytic amount of a Cu-based condensation/hydrogenation/dehydration catalyst. The relative amounts of MIBC and the mixture of IBHK and TMN are controlled by the reaction temperature, a lower temperature, e.g., 130 C., favoring MIBC alone, and a higher temperature, e.g., 200 C., favoring a mixture of MIBC and IBHK plus TMN.

One hallmark of this invention is to pass MIBK over a copper-based condensation/hydrogenation/dehydration catalyst and, depending on the temperature, make MIBC or a mixture of MIBC and IBHK plus TMN. So rather than two independent operations to manufacture MIBC and supplemental IBHK plus TMN, it can now be completed in a single step in which control of the process temperature is the means for controlling the product mix. The process uses a catalyst that is less expensive than the current nickel-based catalyst, and generates fewer impurities.

BRIEF DESCRIPTION OF THE DRAWINGS

FIG. 6 is a graph reporting a comparison in the production of MIBC over time in hours using two different copper-based catalysts and a nickel-based catalyst.

FIG. 7 is a graph reporting a comparison in the production of total $C_{12}$, i.e., IBHK plus TMN, over time in hours using two different copper-based catalysts.

DESCRIPTION OF THE PREFERRED EMBODIMENT

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture and various temperature and other process parameter ranges.

"Catalytic amount" means an amount necessary to promote the reaction of two components at a detectable level, preferably at a commercially acceptable level.

"Condensation/hydrogenation/dehydration reactive conditions" and like terms means reactive conditions in which one or more reactants undergo condensation and/or hydrogenation and/or dehydration. Condensation is the combination of two molecules or moieties to form a single molecule with the loss of a small molecule, e.g., two MIBK joining to form IBHK plus water. Hydrogenation is the addition of hydrogen to an unsaturated organic compound, e.g., converting MIMIC to MIBC. Dehydration is a chemical reaction that involves the loss of water from one a molecule (it is a subset of elimination reactions), e.g., the conversion of DAA to MSO. In the context of this invention, these conditions typically include a temperature between 90 and 300 C. and a pressure between 0.1 and 1 megapascals (MPa).

"Condensation/hydrogenation/dehydration catalyst" and like terms means a catalyst that will promote simultaneously condensation, hydrogenation and dehydration reactions within a given reaction mass under given condensation/hydrogenation/dehydration reactive conditions.

"Cu-based condensation/hydrogenation/dehydration catalyst" and like terms means a condensation/hydrogenation/dehydration catalyst comprising copper.

Figure 1:
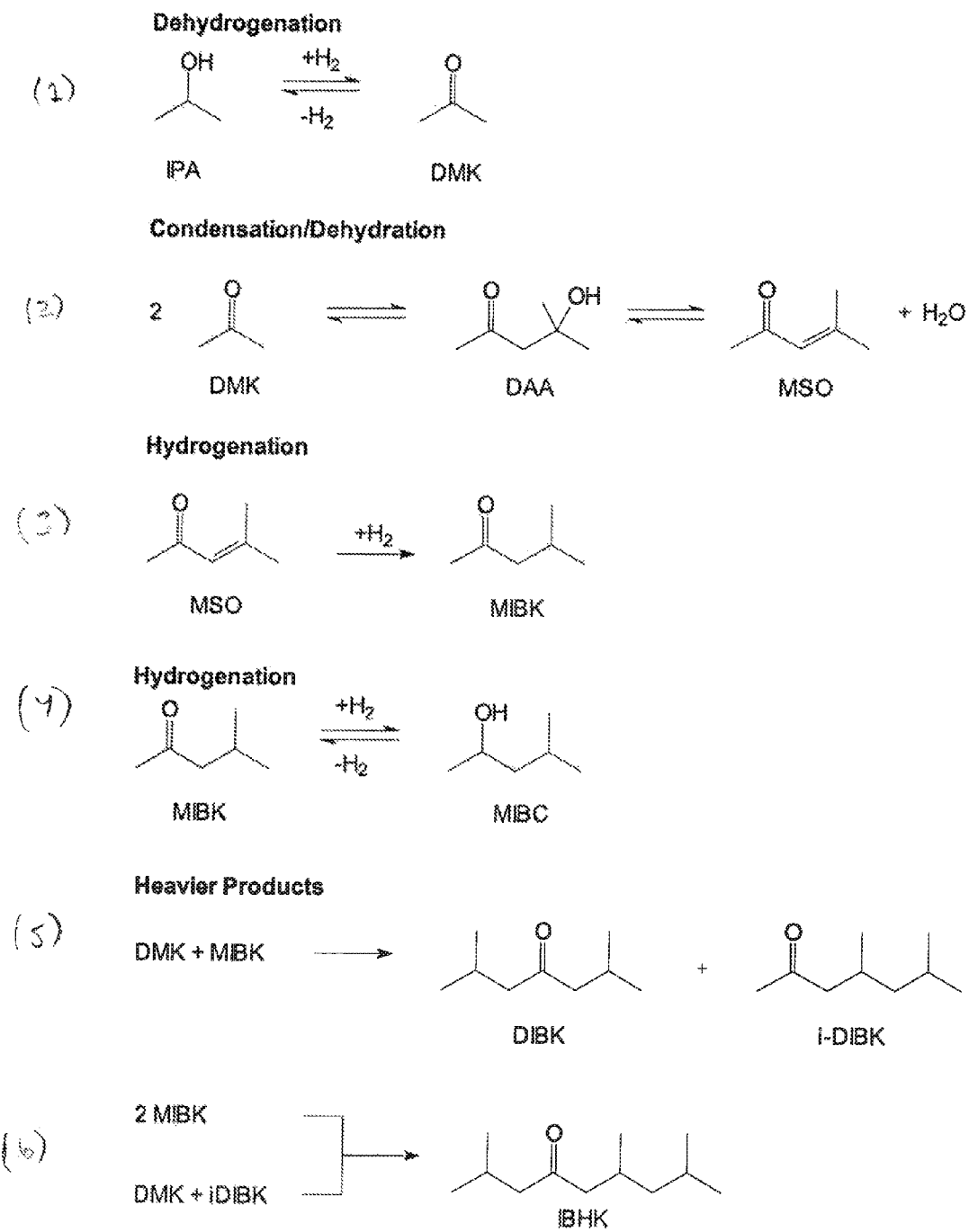
FIG. 1 is a series of reaction equations describing the manufacturing steps for DMK (dimethyl ketone), DAA (diacetone alcohol), MSO, MIBK, MIBC, DIBK, i-DIBK (methyl heptyl ketone) and IBHK.

The production of MIBC and/or a mixture of IBHK and TMN from IPA (isopropyl alcohol) and/or DMK can, in one embodiment, proceed according to the reactions schematically described in FIG. 1. Isomers of MSO, DIBK and other compounds identified in these reaction schemes exist and are probably present in the chemical mix; however, these isomers are not believed to be significant to the instant invention and for purposes of this invention, are considered as normal MSO, DIBK, etc., respectively.

The first three reaction schemes of FIG. 1 describe the conventional preparation of MIBK from IPA and/or DMK. The fourth reaction scheme describes the conventional conversion of MIBK to MIBC that occurs in the mixed ketones converter. This production of MIBC is supplemented with a Ni-based catalyst using MIBK plus hydrogen as the feed.

While bi-functional, copper-based aldol condensation catalysts capable of carrying out hydrogenation/dehydrogenation chemistry are the preferred catalysts for use in the process of this invention, other copper-based catalysts can also be used. Accordingly, any catalyst useful for the production of MIBK and/or DIBK from IPA and/or DMK can be used in the practice of this invention. Such catalysts often have one or more base metals (e.g., Na, Ca, Mg, Li, and the like) for the condensation chemistry, in combination with one or more metals such as Cr, Ni, Pd or Zn, and the like, for the hydrogenation/dehydrogenation chemistry. The dehydration chemistry is promoted by heat and base metals (as described above) and potentially by the catalyst support, e.g., alumina. The preferred catalysts comprise 10% Cu, 1% Ca and 0.5% Cr by weight of the metal, the remainder being the support, preferably alumina. For purposes of the present invention, the composition of the catalyst is not believed to be narrowly critical. For example, the Cu concentration of the hydrogenation catalyst may be 5 to 15% by weight, while the concentration of the base metal (e.g., Ca, Na, Mg, etc.) may be in the range of 0.5 to 3% by weight. With respect to the preferred catalyst composition, Cr is optional and may range from 0 to 1% by weight.

Except as is discussed below in connection with the change of temperature to enhance control over the MIBC and IBHK/TMN ratio, choice of reaction temperature, within the temperature operating envelope of the chosen catalyst, can be varied to convenience, and can typically range from 90 to 260° C., preferably 100 to 240° C., more preferably 120 to 200° C. Temperatures above 240° C., depending upon the thermal stability of the specific catalyst in use, are preferably avoided in order to minimize deactivation of the catalyst. Obviously, lower temperatures are preferred for that reason. Also, as temperature increases, equilibrium begins to favor the ketone thus driving the IBHK/TMN and MIBK/MIBC ratios up. Generally, a temperature below 200° C., e.g., 90 to 150° C., favors MIBC production from both kinetic (e.g., limits condensation to $C_{12}$) and thermodynamic perspectives. Temperatures above 200° C., e.g., 200 to 240° C., increase both the total $C_{12}$ production and the IBHK/TMN ratio.

Choice of reaction pressure is not narrowly critical. Operation in the range of 0.1 to 0.3 MPa is preferred. Similarly, flow rate through the reactor is not narrowly critical, and may typically range from 0.1 to at least 5 LHSV, preferably from 0.1 to at least 1.0 LHSV. "LHSV" means liquid hourly space velocity, a commonly used measure which equals the volumetric rate of feed in the liquid state per volume of catalyst, typically measured at atmospheric pressure and in the liquid state. Preferably, the flow rate is in the range of 0.15 to 0.5 LHSV, and more preferably in the range of 0.2 to 0.3 LHSV.

As is apparent from the reaction chemistry outlined above, hydrogen is both a product and a reactant in the system. Preferably an excess of hydrogen is maintained throughout. This condition is conveniently referred to as the hydrogen balance. As will be recognized by those skilled in the art, the desired hydrogen level can be achieved by such process means as feeding fresh hydrogen, or recycling unused or produced hydrogen. Typically, hydrogen is present in a molar ratio to MIBK of at least 7:1, more typically of at least 8:1.

In addition, the system has a certain ability to remove heat. This condition is known as the heat balance. If an excessive amount of MIBK is fed to the system, the exothermic reaction between MIBK and hydrogen will give off an excessive amount of heat, more IBHK plus TMN is produced as a result, deactivation of the catalyst may occur, and the consumption of hydrogen will be excessive. Thus, typically, a manufacturing unit is limited in how much MIBK can be fed without disrupting the hydrogen balance and/or the heat balance to such an extent that the result is unacceptable.

Better control of the reaction is achieved if the overall system is kept within an acceptable heat balance. Thus, the stoichiometry of the reactions, as well as the relevant heats of reaction, needs to be taken into account. For a system which has only MIBK as a raw material, the general rule for an ideal, adiabatic system is that a pound of MIBK can be fed for about every pound of MIBC that is made by the system. This is because the heat for the production of MIBC is about the same amount endothermic as the hydrogenation of MIBK to MIBC is exothermic. This also maintains the hydrogen in excess because one pound/hour of MIBC production consumes about 0.02 pound/hour hydrogen. Most systems are not ideal, of course, so it may be possible to successfully feed more MIBK than would be suggested by this analysis.

As earlier noted, both the MIBC and IBHK/TMN mixture ratio can be controlled by increasing or decreasing the temperature in combination with the use of a Cu-based catalyst. As a theoretical example, if the system is under typical operating conditions and feed composition using a Ni-based catalyst, then the system would produce 90-95% MIBC and little, if any, IBHK plus TMN mixture. The same performance is achieved if the Ni-based catalyst is replaced with a Cu-based catalyst and the system is operated at 130 C. Operate the Cu-based system at 200 C, however, and the system might now produce 50% MIBC and 20% IBHK plus TMN mixture. Historically, to run a Ni-based catalyst system at 200° C.; would limit MIBC production to less than 60 wt % and produce minimal to nil IBHK plus TMN mixture. Moreover, the side reaction impurities would increase dramatically. To produce the equivalent 20 wt % IBHK plus TMN mixture would have required a separate campaign.

The ability to produce MIBC, and simultaneously co-produce IBHK and TMN using Cu-based condensation/hydrogenation/dehydration catalysts instead of Ni-based catalysts under similar process conditions is demonstrated in the following examples. The process of this invention increases the $C_{12}$, i.e., the IBHK plus TMN, capacity, eliminates the need for separate labor intensive campaigns to supplement IBHK plus TMN production, utilizes a less expensive catalyst, lowers conversion cost, and generates fewer hydrocarbon impurities as compared with a Ni-catalyst based process similar in essentially all other aspects.

The following examples further illustrate the invention. Unless otherwise stated, all parts and percentages are by weight.

SPECIFIC EMBODIMENTS

Materials and Equipment

A fixed bed, single-pass, vapor phase reaction system (nominal ½ inch diameter tubing by 10-12 inch bed length) is used to study the condensation/hydrogenation/dehydration of MIBK to MIBC and IBHK plus TMN. All the MIBK feed is from the same source, i.e., plant-generated product recovered from the distillation columns. Ultra-high purity (99.99%) hydrogen from Air-Gas Inc. is co-fed to the reactor. The catalyst bed temperature is within a few (+ or −5) degrees C. of the reported oven temperature. The reactor vapor product is condensed, and liquid samples are taken each working day morning and analyzed with an HP 6890 gas chromatograph. Samples are water-titrated, and all are less than 2 wt %. The chromatogram method uses a flame ionization detector, is calibrated with a standard, and the results are normalized to 100% using the water factor as determined by a Karl Fisher type titrator.

The catalysts used for the screening study are samples produced by Sud-Chemie Inc. Table 1 compares the Cu-based catalysts to the current Ni-based catalyst.

TABLE 1

Catalyst Composition and Properties

| | Cu Catalyst 1 | Cu Catalyst 1* | Cu Catalyst 2 | Ni Catalyst |
|---|---|---|---|---|
| Ni | — | — | — | >20 |
| Cu | 35-50 (as oxide) | 35-50 (as oxide) | 10 | — |
| Zn | 40-55 (as oxide) | 40-55 (as oxide) | — | — |
| Cr | — | — | 0.4 | — |
| Ca | — | — | 1.2 | — |
| Graphite | <5 | <5 | — | — |
| Al2O3 | — | — | balance | balance |
| SA ($m^2/g$) | 30-60 | 30-60 | >200 | >75 |
| Particle size | ¼" × ¼" | ¼" × ¼" | 5 × 8 mesh | 3 × 8 mesh |
| Bulk density (lbs/$ft^3$) | 80-95 | 80-95 | 50 ± 5 | 60 ± 5 |
| Crush strength (lbs) | >7 | >7 | >15 | 15 |
| Shape | cylindrical tablets | cylindrical tablets | sphere | sphere |

*Cu Catalyst 1* (Cu-1*) is identical to Cu Catalyst 1 (Cu-1) except that Cu-1* has 5-15% calcium aluminate as a binder to help maintain its structural strength.

The screening tests are completed over a relatively short time frame to gain a basic understanding of performance potential (1100 hr for the Cu-1 and Cu-1* catalysts, and 650 hr for the Cu Catalyst 2 (Cu-2)), so life cycle is not determined. The catalysts can be regenerated as needed. In a first run Cu-1* is charged to the inlet half of the reactor and Cu-1 is charged in the outlet half of the reactor. The total amount of catalyst charged to the reactor is 20 cc, and the ratio of Cu-1 to Cu-1* is 1:1 by volume. In the next run, the total amount of catalyst charged is also 20 cc but in this instance, all of the catalyst is Cu-2.

Procedures and Results

Although a range of temperatures are tested to determine the hydrogenation activity of the catalysts, condensation potential and product mix flexibility, and efficiency of converting MIBK to MIBC and/or IBHK plus TMN, most all of the other parameters are held constant.

TABLE 2

Reaction Parameters

| Parameter | Quantity |
|---|---|
| Pressure | 20 psig |
| MIBK Rate | 4 cc/hr; 0.2 $hr^{-1}$ LHSV |
| H2:MIBK* | 8:1 molar |

*Molar ratios of 4:1 and 2:1 are also tested for Cu-2.
LHSV = Liquid Hourly Space Velocity measured in the gas phase and at pressure.

Figure 2:
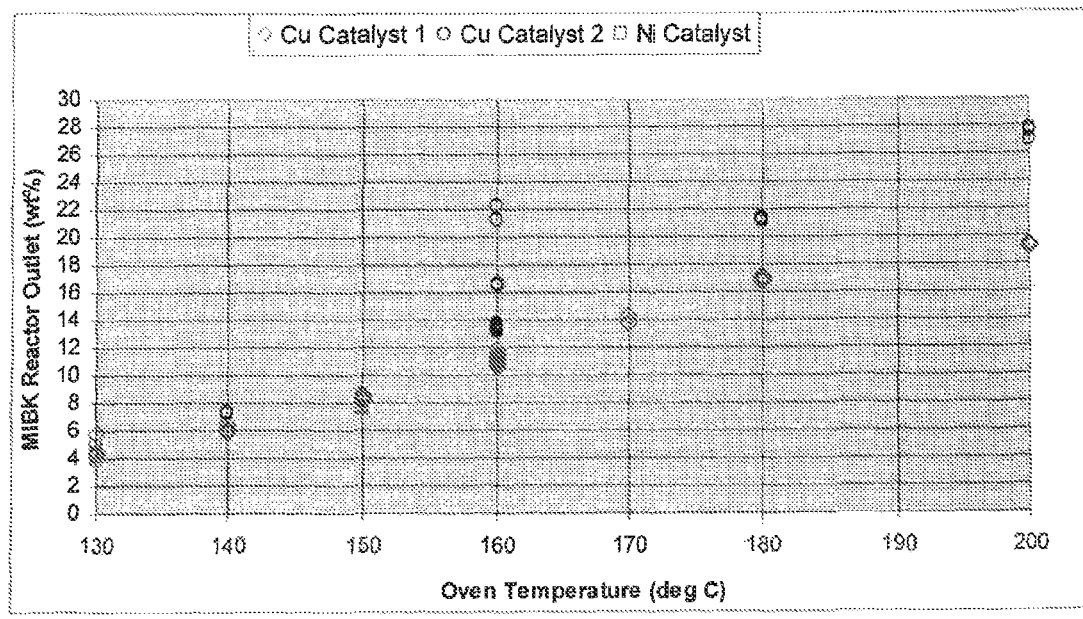
FIG. 2 is a graph reporting the weight percent (wt %) of MIBK in the reactor output as a function of the oven temperature in degrees C.
Figure 3:
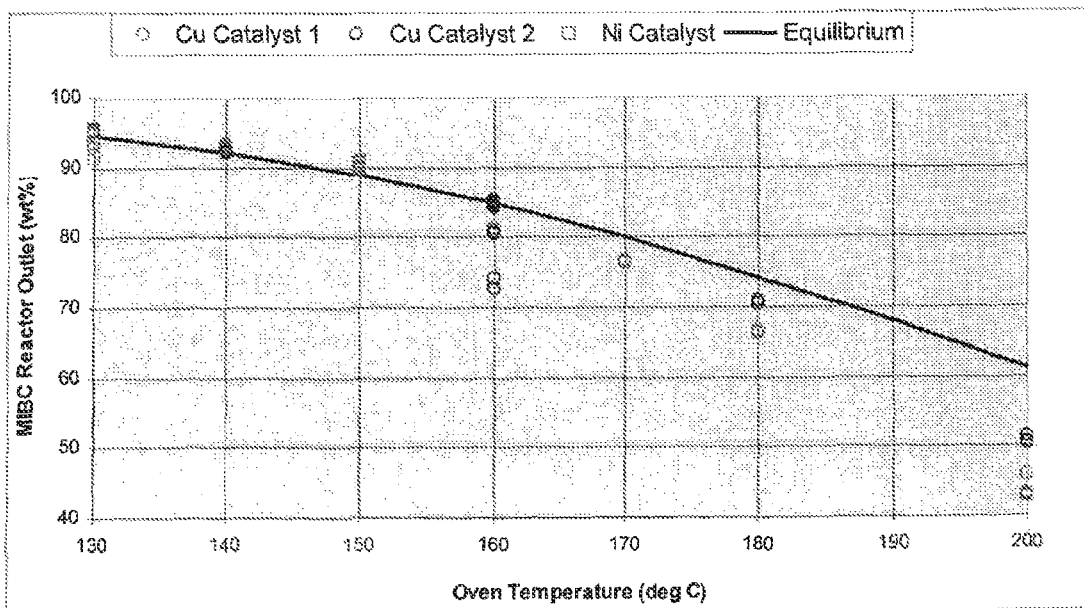
FIG. 3 is a graph reporting the wt % of MIBC in the reactor output as a function of the oven temperature in degrees C.

FIG. 2 shows that the high hydrogen ratio (8:1) pushes the equilibrium conversion to the alcohol as well as prevents capillary condensation which can lead to excessive catalyst deactivation. The results at similar process conditions for the Ni-based catalyst are obtained from a previous study, and are used for comparison purposes.

The major components in the reactor outlet composition are shown in FIGS. 2-5 as a function of the furnace bed temperature. In addition to the results for all three catalysts is the theoretical thermodynamic prediction for MIBC (FIG. 3) when considering only the ketone to alcohol balance (i.e. without condensation). The screening results clearly indicate equilibrium conversion at typical commercial conditions down to 130 C. At the higher temperatures where condensation activity is much greater, MIBC is less than predicted due to MIBK consumption to IBHK plus TMN production. Also the MIBK to MIBC balance is shifted as expected with lower $H_2$:MIBK ratios as is screened with only the Cu-2 catalyst (see FIG. 2) at 160 C. The 8:1 ratio has been historically preferred to prevent capillary condensation which can lead to irreversible structural damage and premature deactivation of the catalyst.

Figure 4:
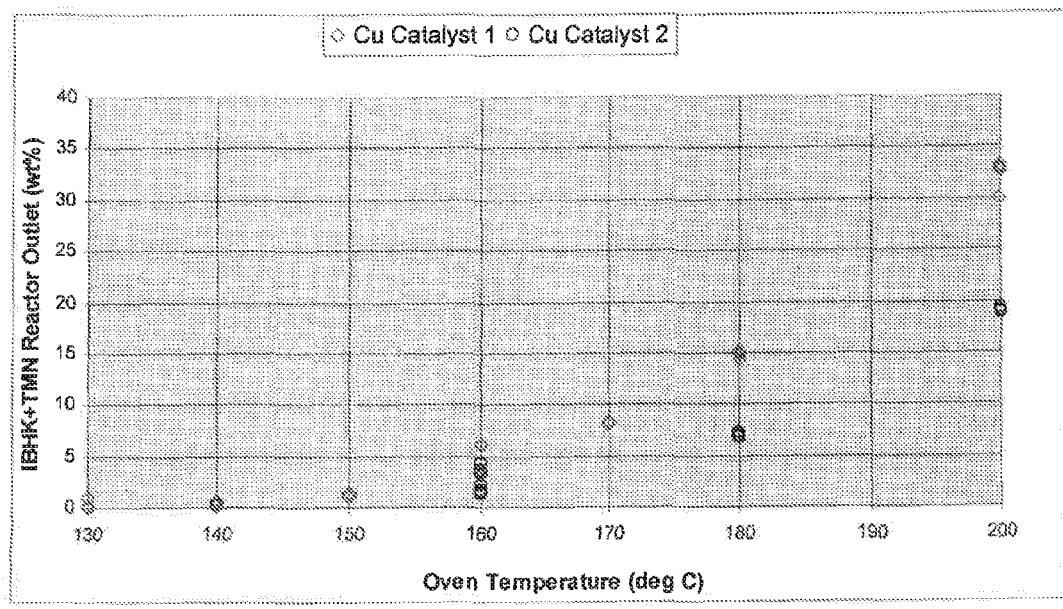
FIG. 4 is a graph reporting the wt % of total $C_{12}$ which equals IBHK plus TMN in the reactor output as a function of the oven temperature in degrees C.
Figure 5:
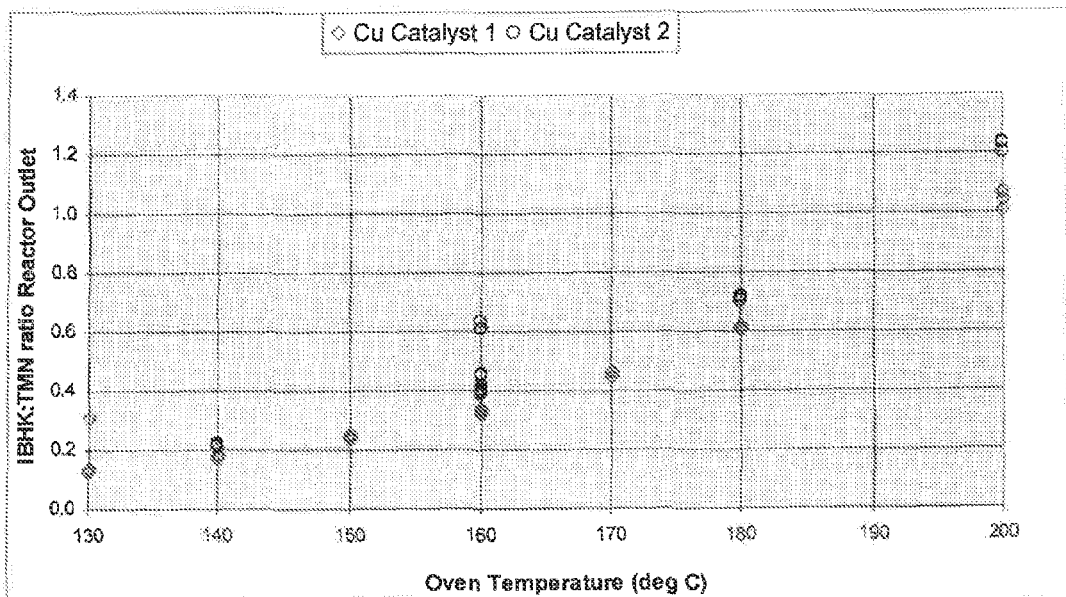
FIG. 5 is a graph reporting the ratio of IBHK to TMN in the reactor output as a function of the oven temperature in degrees C.

FIG. 4 indicates how sensitive IBHK plus TMN production is to temperature. At the lower boundary of 130° C., the total IBHK plus TMN production is about 0.1 wt %. The IBHK plus TMN potential at 200 C is 33% for Cu-1 and Cu-1* and 19% for Cu-2. The Cu-1 and Cu-1* catalysts are more productive as expected compared to the Cu-2 catalyst given that the latter is supported with a lower metal composition (wt % of copper on the catalyst). Also important to note is the ratio of IBHK to TMN as the temperature changes as shown in FIG. 5. In the art, heavier product is comprised mostly of IBHK so the alcohol balance that is obtained by the inventive process is both much greater and more dependent upon the temperature of operation. This balance can be shifted by limiting the hydrogen feed.

The selectivity to product MIBC, IBHK and TMN is typically greater than 98%. Three main impurities are indicated in the gas chromatographic results, i.e., 2-methyl pentane and two other components that are not identified but are likely hydrocarbons. FIGS. 6-7 show typical product range variation of MIBC and IBHK plus TMN as the temperature is varied between 130° C. and 200° C.

Although the invention has been described in considerable detail by the preceding specification, this detail is for the purpose of illustration and is not to be construed as a limitation upon the following appended claims. All U.S. patents, allowed U.S. patent applications and U.S. patent application Publications are incorporated herein by reference.

What is claimed is:

1. A method of increasing the amount of methyl isobutyl carbinol product relative to isobutyl heptyl ketone plus trimethyl nonanol product, both products made from contacting methyl isobutyl ketone with hydrogen and a Cu-based condensation/hydrogenation/dehydration catalyst under condensation/hydrogenation/dehydration reactive conditions which includes a reaction temperature, the method comprising the step of using a reaction temperature of less than 200° C. and the increase measured against a method identical to the method described except that the catalyst is Ni-based rather than Cu-based catalyst.

2. The method of claim 1 in which the reaction temperature is between 90 and 150° C.

3. The method of claim 2 in which the catalyst is a bi-functional copper-based aldol condensation catalyst.

4. The method of claim 3 in which the catalyst comprises one or more of Na, Ca, Mg and Li.

5. The method of claim 4 in which the catalyst further comprises Cr.

6. The method of claim 1 in which the catalyst is carried on a support comprising an aluminum oxide.

7. The method of claim 6 in which the support further comprises calcium aluminate.

8. The method of claim 6 in which the copper is present in an amount of 5 to 15% based on the weight of the catalyst.

9. The method of claim 1 in which the reactive conditions include liquid hourly space velocity of 0.5 to 1.5.

10. The method of claim 1 in which the hydrogen is present in a molar excess relative to the methyl isobutyl ketone.

* * * * *